United States Patent [19]

Fugedi et al.

[11] Patent Number: 5,849,709
[45] Date of Patent: Dec. 15, 1998

[54] SACCHAROPEPTIDES AND DERIVATIVES THEREOF

[75] Inventors: Peter Fugedi; Csaba Peto, both of Alameda, Calif.

[73] Assignee: Glycomed Incorporated, Alameda, Calif.

[21] Appl. No.: 438,669

[22] Filed: May 10, 1995

[51] Int. Cl.$^6$ .......................... A61K 38/04; A61K 31/70
[52] U.S. Cl. ................................ 514/17; 514/18; 514/19; 514/23; 530/322; 536/1.11; 536/53; 536/55; 536/55.2
[58] Field of Search ............................. 530/322; 514/23, 514/17, 18, 19; 536/53, 1.11, 55, 55.2

[56] References Cited

U.S. PATENT DOCUMENTS 5,008,247  4/1991  Meinetsberger .......................... 514/23

FOREIGN PATENT DOCUMENTS 9504751  2/1995  WIPO .

OTHER PUBLICATIONS

Yoshimura et al., "Aminosugars. XXVI. Synthesis of Amido–Bonded Disaccharides Containing Hexosaminuronic Acids", Bull. Chem. Soc. Japan, Vol. 49, pp. 2511–2514, 1976.
Berg et al., "A Carbohydrate Domain Common to Both Sialyl Le$^a$ and Sialyl Le$^x$ is Recognized by the Endothelial Cell Leukoycte Adhesion Molecule ELAM–1," J. Biol. Chem. 266:14865–14872.
Defrees et al., "Ligand Recognition by E–Selectin: Analysis of Conformation and Activity of Synthetic Monomeric and Bivalent Sialyl Lewis X Analogs," J. Am. Chem. Soc. 115:7549–7550 (1993).
Lockoff et al., "Glycolipids as Immunomodulators: Syntheses and Properties", Agnew Chem. Int. Ed. Engl. 30:1611–1620 (1991).
Musser et al., "Ch. 22—Carbhydrated–based Therapeutics," Burger's Medicinal Chemistry and Drug Discovery, Fifth Edition, vol. 1: Principles and Practice, Wolf editor, John Wiley & Sons, Inc., pp. 901–947 (1995).
Oldenburg et al., "Peptide ligands for a sugar–binding protein isolated from a random peptide library," Proc. Natl. Acad. Sci. USA 89:5393–5397 (1992).
Rao et al., "Sialyl Lewis X Minics Derived from a Pharmacophore Search are Selectin Inhibitors with Anti–Inflammatory Activity," J. Biol. Chem. 269(31): 19663–19666 (1994).
Rosen et al., "The selectins and their ligands," Current Opinion in Cell Biology 6:663–673 (1994).
Varki et al., "Selectin ligands," Proc. Natl. Acad. Sci. USA 91:7390–7397 (1994).
Von Roedern and Kessler, "A Sugar Amino Acid as a Novel Peptidomimetic," Angew. Chem. Int. Ed. Engl. 33:687–689 (1994).

Von Roedern and Kessler, "Sugar Amino Acids As Novel Peptidomimetics," Abstract No. A1.12, XVIIth International Carbohydrate Symposium, Ottawa, Jul. 17–22, 1994.
Wittmann et al., "Synthesis and Biological Activity of S– and C– Glycosylated GNRH Agonists," Abstract No. C2.32, XVIIth International Carbohydrate Symposium, Ottawa, Jul. 17–22, 1994.
Yoshimura et al., "Aminosugars. XXVI. Synthesis of Amido–bonded Disaccharides Containing Hexosaminuronic Acids," Bull. Chem. Soc. Japan 49:2511–2514 (1976).
Nicolaou et al., "Carbonucleotoids and Carbopeptides: New Carbohydrate Oligomers", Tetrahedron Letters, vol. 36, No. 11, pp. 1775–1778 (1995).
von Roedern, et al., Angew. Chem. Int. Ed. Engl., 33(6):687–689 (1994).
Yoshimura, et al., Bull. Chem. Soc. Jap., 49(9):2511–2514 (1976).
Nicolaou, et al., Tetrahedron Letters, 36(11):1775–1778 (1995).
Fuchs, et al., Chem. Ber. 108:2254–2260 (1975).
Müller, et al., J. Chem. Soc. 2425–2426 (1995).
Brossmer, et al., Methods in Enzymology 247:153–176 (1994).
Chem. Abstracts 66(15): No. 65793t (1967).
Izv. Akad. Nauk. SSSR, Ser Khim. 8:1400–4 (1966).
Coutsogeorgopoulos, et al. J. Med. Chem. 18(8): 771 (1975).

Primary Examiner—Cecilia J. Tsang
Assistant Examiner—Anish Gupta
Attorney, Agent, or Firm—Lyon & Lyon LLP

[57] ABSTRACT

Saccharopeptides and methods of using the novel saccharopeptides are described having the following structural formula I:

$$W—[—Y—W—]_m \qquad (I)$$

wherein W is independently one or more saccharide(s); Y is independently —CO—NH— or —NH—CO—; and m is an integer greater than or equal to one; or structural formula II:

$$W—Y—[W—X—W—Y]_n—W \qquad (II)$$

wherein W is independently one or more saccharide(s); S is a difunctional or polyfunctional alkyl, aryl or aralkyl group, lipid, amino acid or peptide capable of covalently joining together said saccharides; Y is independently —CO—NH— or —NH—CO—; and n is an integer greater than or equal to zero; or formula III:

$$W—Y^1—X^1—Y^2—W \qquad (III)$$

wherein W is independently one or more saccharide(s); $X^1$ is a difunctional or polyfunctional alkyl, aryl or aralkyl group capable of covalently joining together said saccharides; $Y^1$ is —NH—CO—; and $Y^2$ is —CO—NH—.

3 Claims, No Drawings

SACCHAROPEPTIDES AND DERIVATIVES THEREOF

FIELD OF THE INVENTION

The present invention relates to a novel class of carbohydrate derivatives, saccharopeptides, and to methods for using these saccharopeptides including purification of proteins, and as drugs to treat certain diseases.

BACKGROUND OF THE INVENTION

Naturally occurring carbohydrates occur either in the form of free sugars, or as monosaccharide units linked to other components, such as other sugars (forming oligo- and polysaccharides), proteins (glycoproteins), lipids (glycolipids) or other organic molecules (e.g. nucleosides, steroid glycosides, flavonoids etc.). The sugars (monosaccharides) are attached to each other or to other types of compounds by glycosidic linkage. Most commonly this is an O-glycosidic linkage, but heteroatom substitutions (S, N, C) both exocyclically and endocyclically are also encountered.

Chemical synthesis of biologically active carbohydrate derivatives has been concentrated so far on glycosidically bound compounds. Despite advances in synthetic methodologies, there is still no general solution for the stereoselective formation of glycosidic bonds. This lack of stereoselectivity presents a major obstacle in generating oligosaccharide libraries.

There are scattered examples of synthetic compounds in the literature where monosaccharides are linked to each other by linkages other than the glycosidic bond. These include examples of disulphide (Whistler, R. L., et al., *J. Org. Chem.* (1964) 29:1259), hydrazine (Freudenberg, K., et al., *Ber. Dtsch. Chem. Ges.* (1925) 58:294), carbodiimide (Kovacs, J., et al., *Carbohydr. Res.* (1987) 166:101), carbamide (Jones, A. S., et al., *Tetrahedron* (1962) 18:189), and thiocarbamide (Avalos, M., et al., *J. Chem. Soc. Perkin Trans. I* (1990) 495, and references therein) bridges. However, these examples are limited to pseudo-disaccharides, and in most cases the chemistry used for the preparation of these compounds excludes the synthesis of higher homologs.

Recently some researchers have reported the synthesis of glycosylated peptides. (Von Roedem, E. G. and Kessler, H., *Angew. Chem. Int. Ed. Engl,* (1994) 33:687; Von Roedem, E. G. and Kessler, H., Abstract No. A1.12, *XVIIth International Carbohydrate Symposium,* Ottawa, Jul. 17–22, 1994; Wittmann, V., et al., Abstract No. C2.32, *XVIIth International Carbohydrate Symposium,* Ottawa, Jul. 17–22, 1994). However, these examples are limited to modification of the peptide backbone, either to conformationally restrict the peptide, or to increase the metabolic stability of the peptides. There is no showing of saccharides linked to each other via a peptidic linkage in these examples.

European patent 0 312 086 describes sulfated bis aldonic acid derivatives. It is important to note that in these examples the bis aldonic acid derivatives are limited to the open chain form of the carbohydrate moiety.

The present invention relates to a novel class of carbohydrate derivatives, saccharopeptides, that is a saccharide linked to a peptide or other type of compound via a peptide bond, and to methods for using these saccharopeptides including purification of proteins using affinity chromatography, and as drugs, to treat certain diseases.

SUMMARY OF THE INVENTION

The instant invention provides saccharopeptides having therapeutic and/or prophylactic properties; and that can be used for purification of enzymes.

A second aspect of the invention is the description of saccharopeptides of the general formula I:

$$W-[-Y-W-]_m \qquad (I)$$

wherein each

W is independently one or more saccharide(s);

Y is —CO—NH— or —NH—CO—; and m is an integer greater than or equal to one, and the saccharopeptides have a molecular weight up to 10 kDa.

A third aspect of the invention is the description of saccharopeptides of the general formula II:

$$W-Y-[W-X-W-Y]_n-W \qquad (II)$$

wherein each

W is independently one or more saccharide(s);

X is a difunctional or polyfunctional group, preferably alkyl, aryl or aralkyl, lipid, amino acid or peptide groups capable of covalently joining together said saccharides;

Y is —CO—NH— or —NH—CO—; and n is an integer greater than or equal to zero, and the saccharopeptide has a molecular weight up to 10 kDa.

A fourth aspect of the invention is the description of saccharopeptides of the general formula III:

$$W-Y^1-X^1-Y^2-W \qquad (III)$$

wherein

W is independently one or more saccharide(s);

$X^1$ is a difunctional or polyfunctional group, preferably alkyl, aryl or aralkyl groups capable of covalently joining together said saccharides;

$Y^1$ is —NH—CO—; and $Y^2$ is —CO—NH—.

A fifth object of the invention is a description of methods of treating or preventing disease with the saccharopeptides of the invention.

A sixth aspect of the invention is the description of saccharopeptides that can be beneficially applied to the treatment or prevention of certain diseases including cancer, cardiovascular disease, retinopathies, inflammation, and diseases of viral origin, and preferably diseases that are benefitted by treatment with heparin.

A seventh aspect of the invention is the description of saccharopeptides that can be used for purification of proteins, including enzymes using affinity chromatography.

These and other aspects of the invention will become apparent to a practitioner of this art upon a full consideration of the disclosure presented below.

Description of Specific Embodiments

All publications and patent applications discussed or cited herein are understood to be incorporated by reference to the same extent as if each individual publication or patent application was specifically and individually set forth in its entirety.

The present invention relates to saccharopeptides of the general formula I:

$$W-[-Y-W-]_m \qquad (I)$$

wherein each W is independently one or more saccharide(s) having hydroxyl or amine groups and certain of these groups are optionally substituted; Y is —CO—NH— or —NH—CO—; m is an integer greater than or equal to one, and the saccharopeptide has a molecular weight up to 10 kDa; preferably m=1–5 and W is preferably glucose, galactose, glucosamine, galactosamine, glucuronic acid, galacturonic acid, glucosamine uronic acid, neuraminic acid, maltose or cellobiose; most preferably m=1–2 and W is glucuronic acid.

A second embodiment of the invention are saccharopeptides of the general formula II:

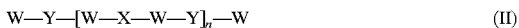

W—Y—[W—X—W—Y]$_n$—W    (II)

wherein each W is independently one or more saccharide(s) having hydroxyl or amine groups and certain of these groups are optionally substituted; X is a difunctional or polyfunctional group, preferably a alkyl, aryl or aralkyl, lipid, amino acid or peptide group capable of covalently joining together said saccharides; Y is —CO—NH— or —NH—CO—; and n is an integer greater than or equal to zero, and the saccharopeptide has a molecular weight up to 10 kDa; preferably n=0–2, and X is preferably ethylene glycol, amino acid and peptides.

A third embodiment of the invention are saccharopeptides of the general formula III:

W—Y$^1$—X$^1$—Y$^2$—W    (III)

wherein each

W is independently one or more saccharide(s);

X$^1$ is a difunctional or polyfunctional group, preferably alkyl, aryl or aralkyl groups capable of covalently joining together said saccharides;

Y$^1$ is —NH—CO—; and

Y$^2$ is —NH—CO—.

With regard to W, in general formula I, II or III, the saccharide(s) can be in the pyranose or furanose ring form and have either an α or β configuration at the anomeric center; and when W is more than one saccharide, said saccharides are independently covalently linked by an ether, thioether, glycosidic, thioglycosidic, amino or amido bond. Further, W can be the same or different saccharide(s), wherein the hydroxyl or amine groups are optionally substituted with H, halogen, —COOH or OR$^1$, where R$^1$ is an alkyl, aryl, aralkyl, acyl, —SO$_3$, —PO$_3$, protecting group, lipids, amino acid and peptide chain.

Examples of monosaccharides useful in the present invention include, but are not limited to, D-glucose, D-galactose, D-mannose, D-xylose, D- and L-arabinose, D-ribose, L-rhamnose, L-fucose, D-glucuronic acid, D-galacturonic acid, L-iduronic acid, D-glucosamine, D-galactosamine, D-lyxosamine, glucosamine uronic acid and sialic acid. Examples of disaccharides useful in the present invention include, but are not limited to, maltose, lactose, cellobiose, melibiose and 3-O-β-D-galactopyranosyl-D-arabinose. Examples of trisaccharides and higher oligosaccharides useful in the present invention include, but are not limited to, maltotriose, and maltotetraose.

In general formula II, X can be a difunctional or polyfunctional alkyl, aryl or aralkyl group, lipid, amino acid or peptide capable of lining two saccharide units together through preferably either an ether, thioether, glycosidic, thioglycosidic, amino or amido bond. Examples include but are not limited to diols, oligomers of diols, aromatic diols such as hydroquinone and dihydroxynapthalenes, aralkyl diols such as benzenedimethanol, dithiols, oligomers of dithiols and thiohydroxy compounds, diamines, oligomers of diamines, dicarboxylic acids and oligomers of dicarboxylic acids. Optionally, the group may possess additional functional groups such as hydroxyls, thiols, amines, carboxylic acids, amides or sulfonic acids wherein these groups do not form bonds with the saccharide units. In the case where n is greater than 0, the saccharopeptide contains more than one X group. When a saccharopeptide contains more than one X group, the same group need not be used throughout the saccharopeptide. Further, when more than one X group is present in a saccharopeptide, each X group—saccharide linkage can be either an ether, thioether, glycosidic, thioglycosidic, amino or amido bond.

In general formula III, X$^1$ can be a difunctional or polyfunctional alkyl, aryl or aralkyl group capable of linking two saccharide units together through an amido bond. Examples include but are not limited to diols, oligomers of diols, aromatic diols such as hydroquinone and dihydroxynapthalenes, aralkyl diols such as benzenedimethanol, dithiols, oligomers of dithiols and thiohydroxy compounds, diamines, oligomers of diamines, dicarboxylic acids and oligomers of dicarboxylic acids. Optionally, the group may possess additional functional groups such as hydroxyls, thiols, amines, carboxylic acids, amides or sulfonic acids.

Attachment of the saccharides to each other by amide linkages can be achieved by the reaction of the amino and carboxylic acid groups, Y in formula I and II, or Y$^1$ and Y$^2$ in formula III, wherein the amino and carboxylic acid groups, respectively, can be attached either directly, or through a X group, to the sugar rings. Besides the amino and/or carboxylic acid substituents, the sugar rings may optionally be additionally substituted, with H, halogen, —COOH or OR$^1$, where R$^1$ is an alkyl, aryl, aralkyl, acyl, —SO$_3$, —PO$_3$, protecting group, lipids, amino acid and peptide chain. Further chain extension via peptide bonds is possible either with the above type carbohydrate derived amino acids (saccharo-amino acids), or with natural or non-proteic amino acids.

Functionalization of monosaccharides to have the above two functional groups, giving the saccharo-amino acids can be accomplished by using the standard methodologies of carbohydrate chemistry (Boger, J. et al., *Helvetica Chimica Acta.* (1978) 61:2190, de Nooy, A. E. J. et al., *Carbohydrate Research,* (1995) 269:89). Two types of saccharoamino acids are represented by the general formulae IV and V. In the saccharo-amino acids of what hereinafter will be referred to as type A (formula IV), the amino and carboxylic groups are attached to different positions of the mono or oligosaccharide unit. Both functional groups can be attached directly to the sugar ring, or alternatively, one or both of them can be linked to the sugar by a X group, wherein p is greater or equal to zero. In compounds of what hereinafter will be referred to as type B (formula V) both the amino and the carboxylic groups are attached to the same carbon of the sugar ring, either directly or by a X group, wherein p is greater or equal to zero.

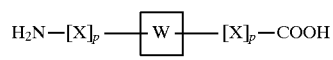

H$_2$N—[X]$_p$——| W |——[X]$_p$—COOH

IV-Saccharo-amino acid (A)

-continued

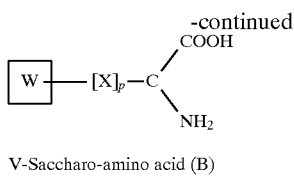

V-Saccharo-amino acid (B)

Synthesis of saccharo-amino acids of either type A and/or B is achieved by converting a hydroxyl group with an amino group and another hydroxyl group with a carboxylic group.

Introduction of an amino group can be achieved by a variety of ways, such as (a) converting the hydroxyl group into a leaving group, and further substituting the leaving group with an appropriate amino functionality. This approach involves conversion of hydroxyl group into a halogen or sulphonyloxy leaving group, preferably bromide, iodide, p-toluenesulphonate, p-bromobenzenesulphonate, methane-sulphonate, trifluoromethane-sulphonate, followed by displacement of the leaving group with a suitable nitrogen containing nucleophile such as ammonia, hydrazine or azide. Azide is the preferred nucleophile, because of the dual advantage of ease of synthesis and the possibility of further modification of the other hydroxyl groups.

(b) Direct replacement of hydroxyl group with an azide, such as treatment with triphenlyphosphine and lithium azide (Boger, J. et al., *Helvetica Chimica Acta.* (1978) 61:2190).

(c) Opening of epoxides with a suitable nitrogen containing nucleophile such as ammonia, azide and other amines under relatively mild conditions also provides a convenient route to synthesize amino sugars.

(d) Glycosyl amines can also be easily synthesized from free sugars using ammonium-hydrogencarbonate or the appropriate protected anomerically pure glycosyl azides.

The carboxylic group can be introduced by the oxidation of the primary alcohol group to a carboxylic acid by standard oxidation methodology, preferably Jones oxidation (Bowers, A. et al.,*J. Chem. Soc.,* (1953) 26:2576), platinum oxidation (Heyns, K. et al, *Ber. Dtsch. Chem. Ges.,* (1955) 88:188) or TEMPO-mediated oxidation (de Nooy, A. E. J. et al., *Carbohydrate Research,* (1995) 269:89), or a single unprotected hydroxyl group can be alkylated with a carboxylic acid containing group.

Coupling of these compounds to give saccharopeptides of the general structural formulae I and II can be accomplished by the standard methodologies of peptide chemistry using derivatives in which the amino group in one reactant and the carboxyl group in the other reactant is in suitable form to react with each other to give a peptide bond, whereas the other functional groups could be protected. Further chain-elongation can be achieved by liberating the amino or the carboxyl group in the resulting product, and coupling it with another mono- or oligomer unit. As mentioned above, the building blocks for chain extension of the saccharo-amino acids include, but are not limited to, carbohydrates, natural amino acids, non-natural amino acids.

Attachment of the X group to the anomeric center of the saccharide unit to form either the glycosidic or thioglycosidic bond can be achieved by the reaction of an activated saccharide derivative, e.g. glycosyl halides, thioglycosides, glycosyl imidates, or n-pentenyl glycosides with the hydroxyl or thiol of the X group. Attachment of the X group by an ether or thioether linkage can be achieved using classical methods of ether preparation.

If so desired, the saccharopeptides can be functionalized to enable the attachment of additional mono or oligosaccharide units.

An additional aspect of the present invention is the sulfation of the saccharide groups preferably via their hydroxyl or amine groups. The hydroxyl and amine groups can be either partially or completely sulfated.

After the saccharide groups have been linked by the X group(s), the saccharide groups are deprotected to yield free hydroxyls and amines. The free hydroxyls and amines are then sulfated using an appropriate sulfating agent such as but not limited to chlorosulfonic acid or complexes of sulfur trioxide with organic bases in an inert solvent such as N,N-dimethylformamide (DMF), hexamethylphosphoric triamide, dimethyl sulfoxide (DMSO) or pyridine. Using techniques known in the art, selective sulfation of either the hydroxyl or amine groups can be obtained. In the case of sulfating amines, water can be used as a solvent. After sulfation, the sulfate groups can be modified to possess biologically acceptable cations, including but not limited to Na, K, Li, Ca, Mg, $NH_4$, aluminum, ethanolamine, triethanolamine, morpholine, pyridine and piperidine.

Saccharopeptides can be synthesized using solid phase synthesis methods. In general, a saccharide with a free amine is selectively protected, preferably with a Boc group by standard methodologies. The Boc-derivative is linked to the Merrifield resin as described by Merrifield. (Merrifield, R. B., *Biochemistry,* (1964) 3:1385; Erickson, B. W. and Merrifield, R. B., *The Proteins,* Neurath, H. and Hill, R. L. (eds), Vol.2, 3rd edn, Academic Press, New York, 255–527; Barany, G. and Merrifield, R. B., *The Peptides,* Gross, E. and Meienhofer, J. (eds), Vol.2, Academic Press, New York, 3–285.)

The Boc group is removed for further elongation, by treating the N-protected, resin linked sugar with an acid, preferably trifluoroacetic acid, to give the free amino resin linked derivative. Coupling the Boc-derivative and the free amino resin linked derivative using the previously described method yields the resin linked protected disaccharopeptide. The protecting groups are removed as described above, and the saccharopeptide is detached from the resin treating it with hydrogen fluoride as described by Merrifield. This method can be repeated to obtain the desired length of the saccharopeptide.

Organic solvents useful for the preparation of the saccharopeptides of the instant invention include but are not limited to DMF, DMSO, 1,4-dioxane, ethyl acetate (EtOAc), hexamethylphosphoric triamide, dichloromethane, tetrahydrofuran (THF) and pyridine. TLC refers to thin layer chromatography.

Certain saccharopeptides synthesized by methods described herein, are described in the Examples below.

Labeled Forms of the Invention Saccharopeptides

The saccharopeptides can be provided with fluorescent, radioisotope, or enzyme labels as desired. Conventional techniques for coupling of label to carbohydrates or related moieties can be used. Such techniques are well established in the art. See, for example, U.S. Pat. No. 4,613,665. The labeled saccharopeptides may be used to identify sites of disease as well as in competitive immunoassays, and as a means to trace the pharmaco-kinetics of the compounds in vivo. Suitable radioisotope labels for this purpose include hydrogen[3], iodine[131], indium[111], technetium[99], and phosphorus[32]. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art.

Administration and Use

The saccharopeptides of the instant invention are useful as inhibitors of β-glucuronidase. β-Glucuronidase is one of the most important enzymes involved in carbohydrate metabolism, and is widespread in mammalian tissues and body fluids, as well as in lower bacteria. Synthetic inhibitors of this enzyme aid in metabolic studies, along with providing a useful tool for purifying the enzyme by affinity chromatography (Y. C. Lee, et al., *Carbohydrate Research*, (1978) 64:302). However, very few inhibitors of β-glucuronidase have been reported. The saccharopeptides of the instant invention are inhibitors of β-glucuronidase, and are useful in the purification of the enzyme by affinity chromatography.

Generally, enzyme activity is determined by measuring adsorption value of various aglycons (e g., phenolphthalein), which are liberated from glucuronic acid by the action of β-glucuronidase during the reaction.

The β-glucuronidase inhibition assay is preferably performed in a solvent. Examples of the solvent include water and a suitable buffer, preferably an acetate or an AMP (2-amino-2-methyl-1-propanol) buffer. Phenolphthalein mono-β-glucuronic acid and a saccharopeptide substrate are treated with the enzyme at room temperature, at a pH of about 4–5. The reaction period ranges from 0.5–2 hours. After completion of the reaction, the enzymic reaction is stopped by adjusting the pH and the absorbance is measured at 550 nm.

The saccharopeptides of the instant invention are also useful in therapeutic applications for treating or preventing a variety of diseases including cancer, inflammation, and diseases caused or exacerbated by platelet aggregation or angiogenic activity.

Administration of the saccharopeptides of the invention is typically by routes appropriate for glycosaminoglycan compositions, and generally includes systemic administration, such as by injection.

Particularly preferred is intravenous injection, as continuous injection over long time periods can be easily continued. Also preferred are introduction into the vascular system through intraluminal administration or by adventitial administration using osmotic pumps or implants. Typical implants contain biodegradable materials such as collagen, polylactate, polylactate/ polyglycoside mixtures, and the like. These may be formulated as patches or beads. Typical dosage ranges are in the range of 0.1–10 mg/kg/hr on a constant basis over a period of 5–30, preferably 7–14, days. Particularly preferred dosage is about 0.3 mg/kg/hr, or, for a 70 kg adult, 21 mg/hr or about 500 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Pharmaceutical Sciences,* Mack Publishing Company, Easton, Pa., latest edition.

The saccharopeptides may also be labeled using typical methods such as radiolabeling, fluorescent labeling, chromophores or enzymes, and used to assay the amount of such compounds in a biological sample following its administration. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention, as described below, are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

The synthesis and biological activity of the saccharopeptides are illustrated in the following examples. Further objectives and advantages other than those set forth above will become apparent from the examples.

EXAMPLES

Example 1

Synthesis of N-(D-glucopyran-1-osyl uronic acid)-1-azido-1-deoxy-β-D glucopyranuronamide (9α and 9β)

Methyl {2,3,4-tri-O-acetyl-β-D-glucopyranosyl azide}uronate (1)

Methyl {2,3,4-tri-O-acetyl-α-D-glucopyranosyl bromide}uronate (8 g) was dissolved in DMF (100 ml) and a 1:1 mixture of sodium azide (3.25 g):lithium azide (2.25 g) was added into the solution. The mixture was stirred overnight at room temperature and was diluted with chloroform (500 ml) and water. The organic layer was washed with water and evaporated. The residue was crystallized from ethanol to yield 1 (6.67 g, 92%). $[\alpha_D]$–33.4° (c 1.00, chloroform); $^1$H-NMR data (CDCl$_3$): δ2.03, 2.04, and 2.08 (3s, 3H, 3 COCH$_3$), 3.78 (s, 3H, COOCH$_3$), 4.13 (d, 1H), 4.73 (d, 1H, H-1 $J_{1,2}$=8.7 Hz), 4.97 (t, 1H), 5.25 (m, 2H). $^{13}$C-NMR data (CDCl$_3$): δ20.5, 20.6 (3C, COCH$_3$), 53.1 (COOCH$_3$), 69.0, 70.4, 71.8, 74.2 (4C, C-2,3,4,5), 88.1 (C-1), 166.5 (COOCH$_3$), 169.1, 169.3, 170.0 (3C, COCH$_3$).

Methyl {2,3,4-tri-O-acetyl-β-D-glucopyranosyl amine}uronate (2)

A solution of 1 (0.48 g) in EtOAc (10 ml) was hydrogenated in the presence of 10% palladium on carbon (Pd-C, 0.1 g) at room temperature and atmospheric pressure for one hour. The catalyst was filtered off and the filtrate was concentrated to a syrup 2 (0.44 g, 100%). $^1$H-NMR data (CDCl$_3$): δ2.02, 2.06 (2s, 9H, 3 COCH$_3$), 3.74 (s, 3H, COOCH$_3$), 4.04 (d, 1H), 4.25 (d, 1H), 4.87 (t, 1H), 5.17 (m, 1H), 5.31 (t, 1H). $^{13}$C-NMR data (CDCl$_3$): δ20.5, 20.6, 20.8 (3C, COCH$_3$), 52.9 (COOCH$_3$), 61.0, 71.7, 72.4, 73.5 (4C, C-2,3,4,5), 85.3 (C-1).

2,3,4-Tri-O-acetyl-1-azido-1-deoxy-β-D-glucopyranuronic acid (6)

(a) To a solution of 2,3,4,6-tetra-O-acetyl-β-D-glucopyranosyl azide (3, 5.6 g) in methanol (50 ml) 1M methanolic sodium methoxide (0.5 ml) was added and the solution was stirred overnight at 0° C., then it was neutralized with AG 50W-X8 (H+) ion-exchange resin. The resin was filtered off, the filtrate was evaporated and dried in vacuo to give the known β-D-glucopyranosyl azide (4).

Composition 4 (3.05 g) was dissolved in dry pyridine (50 ml), chlorotriphenyl-methane (5.01 g) was added and the reaction mixture was stirred at 70° C. for three hours. It was cooled to 0° C., acetic anhydride (6.36 ml) was added dropwise and the mixture was stirred overnight at room temperature. It was poured into ice-water and was diluted with chloroform (300 ml). The organic layer was washed subsequently with water, 2M hydrochloric acid, water, was dried and evaporated to leave 2,3,4-tri-O-acetyl-6-O-trityl-β-D-glucopyranosyl azide (5, 7.67 g, 90%).

Jones oxidation of composition 5 (7.67 g) in acetone (70 ml) with a solution of chromium trioxide (8.02 g) in 3.5M sulfuric acid (10 ml) afforded the acid 6 which was purified by column chromatography to give 2.86 g (62%) final product. $[\alpha_D]$-12.80 (c 1.00, methanol), $^1$H-NMR data (CD$_3$OD): δ1.98, 2.00, 2.05 (3s, 9H, COCH$_3$), 4.25 (d, 1H), 4.95 (m, 2H,), 5.19 (t, 1H), 5.34 (t, 1H). $^{13}$C-NMR data (CD$_3$OD): δ20.5, 20.6 (3C, COCH$_3$), 70.7, 72.0, 73.7, 75.4 (C-2,3,4,5), 88.8 (C-1), 170.9, 171.1, 171.4 (3C,COCH$_3$).

(b) Selective deesterification of (1) (371 mg) with lithium iodide (670 mg) in pyridine (5 ml) gave the free carboxylic acid (6) (165 mg, 47%).

N-{Methyl 2,3,4-tri-O-acetyl-D-glucopyran-1-osyl uronate}-{1-azido-1-deoxy-2,3,4-tri-O-acetyl-β-D-glucopyranuronamide} (7α and 7β)

(a) Compositions 2 (0.432 g) and 6 (403 mg) were dissolved in DMF (5 ml) and N-isobutoxycarbonyl-2-isobutoxy-1,2-dihydroquinoline (IIDQ) (385 μl) was added dropwise into the solution. The reaction mixture was stirred at room temperature until the free carboxylic acid derivative was consumed. The solvent was evaporated and the residue was purified by column chromatography (toluene-acetone, 9:1→85:15) to yield N-{Methyl 2,3,4-tri-O-acetyl-β-D-glucopyran-1-osyl uronate}-{1-azido-1-deoxy-2,3,4-tri-O-acetyl-β-D-glucopyranuronamide} (7β, 248 mg, 31%). $[\alpha_D]$ -8.7° (c 0.98, chloroform); $^1$H-NMR data (CDCl$_3$): δ2.02, 2.04, 2.05, 2.09, 2.16 (5s, 18H, COCH$_3$), 3.73 (s, 3H, COOCH$_3$), 3.98, 4.13 (2d, 2H, H-5,5'), 4.68 (d, 1H, H-1, $J_{1,2}$=8.9 Hz), 4.94 (t, 1H), 4.95 (t, 1H), 5.00 (t, 1H), 5.13 (d, 1H, H-1', $J_{1',2'}$=9.5 Hz), 5.18 (t, 1H), 5.41 (t, 1H), 7.34 (d, 1H, NH). $^{13}$C-NMR data (CDCl$_3$): δ20.4, 20.5, 20.5, 20.6 (6C, COCH$_3$), 52.9 (COOCH$_3$), 68.8, 69.6, 70.0, 70.5, 71.7, 71.7, 73.0, 73.9 (8C, C-2,3,4,5,2',3',4',5'), 77.6 (C-1'), 88.0 (C-1), 166.7, 167.2 (2C, CONH and COOCH$_3$), 169.3, 169.5, 169.6, 169.6, 169.8, 171.2 (6C, COCH$_3$).

The α isomer, N-{methyl 2,3,4-tri-O-acetyl-α-D-glucopyran-1-osyl uronate}-{1-azido-1-deoxy-2,3,4-tri-O-acetyl-β-D-glucopyranuronamide} (7α) eluted second (248 mg, 31%). $[\alpha_D]$+6.0° (c 1.00, chloroform); $^1$H-NMR data (CD$_3$OD): δ1.97, 1.98, 2.03, 2.04, 2.06 (5s, 18H, COCH$_3$), 3.72 (s, 3H, COOCH$_3$), 4.28 (d, 1H), 4.45 (d, 1H, H-1, $J_{1,2}$=8.6 Hz), 5.00–5.07 (m, 2H), 5.07 (t, 1H), 5.12 (t, 1H), 5.32 (d, 1H), 5.34 (d, 1H), 5.67 (t, 1H), 5.96 (d, 1H, H-1', $J_{1',2'}$=5.1 Hz). $^{13}$C-NMR data (CD$_3$OD): δ20.5, 20.5, 20.5, 20.6 (6C, COCH$_3$), 53.1 (COOCH$_3$), 69.7, 70.0, 70.2, 70.3, 71.2, 71.7, 73.5, 74.6, 76.6 (9C, C-2,3,4,5,1',2',3',4',5'), 88.9 (C-1), 169.1 (CONH and COOCH$_3$), 170.7, 171.0, 171.1, 171.2 (6C, COCH$_3$).

(b) Coupling of 2 and 6 using N,N-diisopropyl-carbodiimide (DIC) instead of IIDQ afforded 7α and 7β in a better combined yield (592 mg, 74%) in the same ratio as above.

(c) Coupling of 2 and 6 using THF as a solvent instead of DMF afforded 7β exclusively (Yield 87%).

N-(Methyl-D-glucopyran-1-osyl uronate)-(1-azido-1-deoxy-β-D-glucopyranuronamide) (8α and 8β)

To a solution of 7β (66 mg) in methanol (5 ml) 1M methanolic sodium methoxide (0.2 ml) was added and the solution stirred at 0°–5° C. The deacetylated product crystallized from the solution. The product was filtered off and washed with cold methanol to furnish N-(methyl β-D-glucopyran-1-osyl uronate)-(1-azido-1-deoxy-β-D-glucopyranuronamide) (8β, 39 mg, 96%). $^1$H-NMR data (D$_2$O): δ3.33 (t, 1H, H-2), 3.51–3.64 (m, 5H, H-3,4,2',3',4'), 3.82 (COOCH$_3$), 4.04, 4.18 (2d, 2H, H-5,5'), 4.85 (d, 1H, H-1, $J_{1,2}$=8.8 Hz), 5.13 (d, 1H, H-1', $J_{1',2'}$=8.7 Hz). $^{13}$C-NMR data (D$_2$O): δ53.4 (COOCH$_3$), 71.2, 71.3, 71.4, 72.5, 75.4, 76.1, 76.3, 76.9 (8C, C-2,3,4,5,2',3',4',5'), 79.4 (C-1'), 90.4 (C-1), 171.1, 171.5 (2C, COOCH$_3$, NHCO).

Composition 7α was deacetylated as described above. The reaction mixture was neutralized with AG 50W-X8 (H+) ion-exchange resin. The resin was filtered off and the solvent was evaporated to give N-(methyl α-D-glucopyran-1-osyl uronate)-(1-azido-1-deoxy-β-D-glucopyranuronamide) (8α, 38 mg, 95%). $[\alpha_D]$+2.8 (c 0.96 H$_2$O); $^1$H-NMR data (D$_2$O): δ3.84 (t, 1H, H-2), 3.55–3.75 (m, 3H), 3.81 (s, 3H, COOCH$_3$), 3.84–3.91 (m, 2H), 4.13, 4.21 (d, 2H, H-5,5'), 4.85 (d, 1H, H-1, $J_{1,2}$=8.7 Hz), 5.73 (d, 1H, H-1', $J_{1',2'}$=4.0 Hz). $^{13}$C-NMR data (D$_2$O): δ53.3 (COOCH$_3$); 68.9, 70.1, 70.1, 71.9, 72.6, 72.8, 75.5, 76.4, 76.7 (C-2,3,4,5,1',2',3',4',5'), 90.4 (C-1), 171.49, 171.51 (2C, COCH$_3$, NHCO).

N-(D-glucopyran-1-osyl uronic acid)-1-azido-1-deoxy-β-D-glucopyranuronamide (9α and 9β)

The deacetylated product 8β (32 mg) was dissolved in 0.1M NaOH (2 ml) and kept overnight at 0°–5° C. The solution was neutralized with AG 50W-X8 (H+) ion-exchange resin, was filtered, and the filtrate was lyophilized to give N-(β-D-glucopyran-1-osyl uronic acid)-1-azido-1-deoxy-β-D-glucopyranuronamide (9β, 30 mg, 97%). $^1$H-NMR data (D$_2$O): δ3.32 (t, 1H, H-2), 3.50–3.62 (m, 5H), 4.03, 4.09 (2d, 2H, H-5,5'), 5.12 (d, 1H, H-1', $J_{1',2'}$=8.8 Hz), the H-1 signal was covered by the signal of HOD. $^{13}$C-NMR data (D$_2$O): δ71.2, 71.3, 71.4, 72.5, 76.2, 76.3 (C-2,3,4,5, 2',3',4',5'), 79.2 (C-1'), 90.4 (C-1), 171.5 (NHCO), 172.7 (COOH).

The deacetylated product 8α (32 mg) was treated in the same way as described above to give N-(α-D-glucopyran-1-osyl uronic acid)-1-azido-1-deoxy-β-D-glucopyranuronamide (9α, 32 mg, 100%). $^1$H-NMR data (D$_2$O): δ3.34 (t, 1H, H-2), 3.55–3.63 (m, 2H), 3.70 (t, 1H), 3.81–3.89 (m, 2H), 4.13, 4.14 (d, 2H, H-5, 5'), 4.84 (d, 1H, H-1 $J_{1,2}$=8.9 Hz), 5.73 (d, 1H, H-1' $J_{1',2'}$=4.4); $^{13}$C-NMR (D$_2$O) δ69.0, 71.0, 72.1, 72.5, 72.6, 75.5, 76.4, 76.7 (C-2,3,4,5,1',2'3'4'5'), 90.5 (C-1), 171.5 (NHCO), 172.7 (COOH).

Example 2

Methyl{methyl 3,4-di-O-acetyl-2-deoxy-2-[(methyl-3,4-di-O-acetyl-2-benzyloxycarbonylamino-2-deoxy-α-D-glucopyranoside uronamido)-α-D-glucopyranoside]}uronate (15)

Methyl 3,4-di-O-acetyl-2-benzyloxycarbonylamino-2-deoxy-α-D-glucopyranosyluronic acid (12)

To a solution of methyl 2-benzyloxycarbonylamino-2-deoxy-α-D-glucopyranoside (10, 6.36 g) in dry pyridine (30 ml) triphenylmethyl chloride (8.12 g) was added. The mixture was stirred at 70° C. for three hours. After cooling to room temperature acetic anhydride (5.49 ml) was added and the mixture was stirred overnight at room temperature. It was poured into ice-water and worked up as described for 7. Column chromatography (toluene-ethyl acetate, 85:15) afforded methyl 3,4di-O-acetyl-2-benzyloxycarbonylamino-2-deoxy-6-O-triphenylmethyl-α-D-glucopyranoside (11, 11.65 g, 96%).

Jones oxidation of composition 11 (11.65 g) in acetone (100 ml) with a solution of chromium trioxide (10.7 g) in 3.5M sulfuric acid (15 ml) after purification by column chromatography gave the acid 12, (5.36 g, 71%). $[\alpha]_D$+66.2 (c 1.03 methanol); $^1$H-NMR data (CD$_3$OD): δ1.81, 1.99 (2s, 6H, COCH$_3$), 3.43 (s, 3H, OCH$_3$), 4.10 (dd, 1H, H-2), 4.14 (d, 1H, H-5), 4.96 (d, 1H, H-1, J$_{1,2}$=3.3 Hz), 5.01 (d, 1H, OCH$_2$), 5.16 (d, 1H, OCH$_2$), 5.18 (t, 1H, H-3), 5.25 (t, 1H, H-4). $^{13}$C-NMR data (CD$_3$OD): δ20.6, 20.9 (2C, COCH$_3$), 54.6 (OCH$_3$), 56.5 (C-2), 67.6 (OCH$_2$Ph), 71.2, 71.5, 72.6 (C-3,4,5), 100.3 (C-1), 128.9, 129.0, 129.4 (aromatic carbons), 138.3 (quaternary aromatic carbon), 158.3 (OCOCH$_2$Ph), 171.6, 171.9 (2C, COCH$_3$), 175.7 (COOH).
Methyl (methyl 3,4-di-O-acetyl-2-amino-2-deoxy-α-D-glucopyranoside)uronate (14)

To a solution of 12 (1.8 g) in dry methanol AG 50W-X8 (H+) ion-exchange resin was added and mixture was stirred overnight. The resin was filtered off and the filtrate was evaporated. The residue was purified by column chromatography (toluene-ethyl acetate, 3:2) to give methyl (methyl 3,4di-O-acetyl-2-benzyloxycarbonylamino-2-deoxy-α-D-glucopyranoside)uronate (13, 1.68 g, 93%). $[\alpha]_D$+92.5 (c 1.04 chloroform); $^1$H-NMR data (CDCl$_3$): δ1.87, 1.99 (2s, 6H, COCH$_3$), 3.40 (s, 3H, OCH$_3$), 3.72 (s, 3H, COOCH$_3$), 4.09 (m, 1H, H-2), 4.25 (d, 1H, H-5), 4.84 (d, 1H, H-1, J$_{1,2}$=3.3 Hz), 5.01 (d, 1H, OCH$_2$), 5.14 (d, 1H, OCH$_2$), 5.16 (t, 1H, H-4), 5.25 (t, 1H, H-3), 5.30 (d, 1H, NH). $^{13}$C-NMR data (CDCl$_3$): δ20.9 (s, 2C, COCH$_3$), 53.2 (COOCH$_3$), 53.9 (C-2), 56.4 (OCH$_3$), 67.3 (OCH$_2$), 69.0 (C-5), 69.9 (C-4), 70.9 (C-3), 99.3 (C-1), 128.5, 128.6, 129.0 (aromatic carbons), 136.9 (quaternary aromatic carbon), 156.2 (OCOCH$_2$Ph), 168.6 (COOCH$_3$), 169.8, 171.1 (COCH$_3$).

A solution of 13 (219 mg) in EtOAc (5 ml) was hydrogenated in the presence of 10% Pd-C (0.1 g) at room temperature and at atmospheric pressure for one hour. The catalyst was filtered off and the filtrate was evaporated to give 14 as a syrup (157 mg, 100%). $[\alpha]_D$+148.3 (c 1.26 chloroform); $^1$H-NMR data (CDCl$_3$): δ1.53 (s, 2H, NH$_2$), 2.02, 2.09 (2s, 6H, COCH$_3$), 2.97 (dd, 1H, H-2), 3.46 (s, 3H, OCH$_3$), 3.75 (s, 3H, COOCH$_3$), 4.29 (d, 1H, H-5), 4.84 (d, 1H, H-1, J$_{1,2}$=3.4 Hz), 5.06 (t, 1H, H-4), 5.17 (t, 1H, H-3). $^{13}$C-NMR data (CDCl$_3$): δ20.6, 20.9 (2s, COCH$_3$), 52.8 (COOCH$_3$), 54.3 (C-2), 56.0 (OCH$_3$), 68.7, 69.9, 73.6 (3C, C-5,4,3), 101.0 (C-1), 168.6 (COOCH$_3$), 169.7, 170.7 (2C, COCH$_3$).

Disaccharopeptide (15)

(a) Compositions 14 (157 mg) and 12 (216 mg) were dissolved in THF (5 ml) and 1-(3-dimethylaminopropyl)-3-ethylcarbodiimide hydrochloride (DEC) (95 mg) and N-hydroxybenztriazole (HOBT) (6 mg) were added. The reaction mixture was stirred overnight at room temperature. The mixture was diluted with water and chloroform (20 ml), the organic layer was separated and was washed with water (2×5 ml) and evaporated. Column chromatography (toluene-acetone, 3:2) gave composition 15 (149 mg, 41%). $^1$H-NMR data (CDCl$_3$): δ1.88, 1.97, 2.01, 2.03 (4s, 12H, COCH$_3$), 3.37, 3.50 (2s, 6H, 2 OCH$_3$), 3.74 (s, 3H, COOCH$_3$), 4.05 (m, 2H, H-2,5), 4.28 (m, 2H, H-2',5'), 4.83 (d, 1H, H-1, J$_{1,2}$=3.6 Hz), 4.85 (d, 1H, H-1', J$_{1',2'}$=3.6 Hz), 5.01 (d, 1H, OCH$_2$), 5.14 (d, 1H, OCH$_2$), 5.00–5.15 (m, 2H, H-3,4), 5.18–5.31 (m, 2H, H-3,4'), 5.33 (d, 1H, NHCOO—CH$_2$Ph), 6.61 (d, 1H, NHCO-amide). $^{13}$C-NMR data (CDCl$_3$): δ20.5, 20.5, 20.6, 20.7 (4C, COCH$_3$), 51.2 (C-2'), 52.8 (COOCH$_3$), 53.8 (C-2), 55.7 (OCH$_3$), 56.1 (OCH$_3$), 67.0 (OCH$_2$), 68.5 (C-5'), 68.6 (C-5), 69.3, 69.6, 70.0, 70.1 (C-3,4, 3',4'), 98.1 (C-1'), 98.6 (C-1), 128.1, 128.3, 128.5 (5C, aromatic carbons), 136.2 (quaternary aromatic carbon), 155.8 (OCOCH$_2$Ph), 167.5 (NHCO-amide), 168.2 (COOCH$_3$), 169.4, 169.8, 170.7, 170.8 (4C, COCH$_3$).

(b) Coupling of 12 and 14 using N,N-diisopropylcarbodiimide (DIC) instead of DEC afforded 15 in a better yield (95%).

Example 3

Trisaccharopeptide (17)

A solution of 15 (430 mg) in EtOAc (15 ml) was hydrogenated in the presence of 10% Pd-C (150 mg) at room temperature and at atmospheric pressure for one hour. The catalyst was filtered off and the filtrate was evaporated to give the partially deprotected disaccharopeptide 16 (350 mg, 100%) and directly used for the coupling reaction.

Compositions 16 (350 mg) and 12 (260 mg) were dissolved in THF (10 ml) and 1,3-diisopropylcarbodiimide (0.1 ml) and HOBT (50 mg) were added into the solution. The reaction mixture was stirred for two days at room temperature. The reaction mixture was worked up as described in Example 16. Column chromatography gave the title product 17 (560 mg, 93%). $[\alpha]_D$+133.9 (c 1.00 chloroform); $^1$H-NMR (CDCl$_3$) δ1.89, 1.97, 2.00, 2.03, 2.04, 2.06 (6s, 18H, COCH$_3$), 3.38, 3.46, 3.51 (3s, 9H, OCH$_3$), 3.76 (s, 3H, COOCH$_3$), 4.01–4.11 (m, 3H, 2×H-2 and H-5), 4.18–4.32 (m, 3H, 2×H-5 and H-2), 4.84 (d, 3H, H-1,1',1", J$_{1,2}$=3.4 Hz), 5.00–5.22 (m, 5H), 5.24–5.35 (m, 4H, incl NH and OCH$_2$Ph), 6.62 (d, 1H, NH), 6.68 (d, 1H, NH), 7.34 (m, 5H, Ph); $^{13}$C-NMR (CDCl$_3$) δ20.5, 20.5, 20.6, 20.7 (6C, COCH$_3$), 51.2, 51.5, 52.8, 53.7, 55.8, 55.8, 56.1 (C-2,2',2", 3 x OCH$_3$, COOCH$_3$), 67.0 (OCH$_2$Ph), 68.4 (2C), 68.8, 69.3, 69.4, 69.6, 69.7, 69.9, 70.1 (C-3,4,5,3',4',5',3",4",5"), 97.8, 98.1, 98.5 (C-1,1',1"), 128.1, 128.2, 128.5 (Ph), 136.2 (q Ph), 155.8 (OCOCH$_2$Ph), 167.6, 167.7 (NHCO-amide), 168.2 (COOCH$_3$), 169.4, 169.8, 169.9, 170.7 (6C, COCH$_3$).

Example 4

Tetrasaccharopeptide (18)

A solution of 17 (320 mg) was hydrogenated as described above, and the free amine (270 mg) was coupled with 12 (130 mg) in a mixture of THF—1,4-dioxane as described above, to give the title composition 18 (280 mg, 72%). $[\alpha]_D$+140.9 (c 1.08 chloroform); $^1$H-NMR (CDCl$_3$) δ1.90, 1.98, 1.99, 2.03, 2.04, 2.06, 2.08 (8s, 24H, COCH$_3$), 3.38, 3.45, 3.49, 3.52 (4s, 24H, OCH$_3$), 3.76 (s, 3H, COOCH$_3$), 4.03–4.12 (m, 4H), 4.19–4.32 (m, 4H), 4.82–4.86 (2d, 4H, H-1,1',1"',1"''), 4.98–5.35 (m, 11H, 8 sugar skeleton, NH and OCH$_2$Ph), 6.62, 6.67, 6.69 (3d, 3H, NH), 7.34 (d, 5H, Ph); $^{13}$C-NMR (CDCl$_3$) δ20.5, 20.6, 20.6, 20.7, 20.7 (8C, COCH$_3$), 51.1, 51.5, 52.9, 53.7, 55.7, 55.8, 56.1 (9C, C-2,2',2", 2"', 4 x OCH$_3$, COOCH$_3$), 67.1 (OCH$_2$Ph), 68.3, 68.4, 68.6, 69.3, 69.5, 69.5, 69.6, 69.9, 70.1 (12C, C-3,4,5, 3',4', 5',3",4",5",3"',4"',5"'), 97.0, 98.1, 98.5 (4C, C- 1,1',1", 1"'), 128.1, 128.3, 128.53 (Ph), 136.1 (q Ph), 155.8 (OCOCH$_2$Ph), 167.6, 167.7, 167.8 (NHCO-amide), 168.2 (COOCH$_3$), 169.5, 169.9, 169.9, 170.6, 170.7, 170.7 (8C, COCH$_3$), FAB-MS (mNBA) m/z [M+H]+1259.0.

The structures of compositions 9, 15, 17 and 18 are shown below in formula VI:

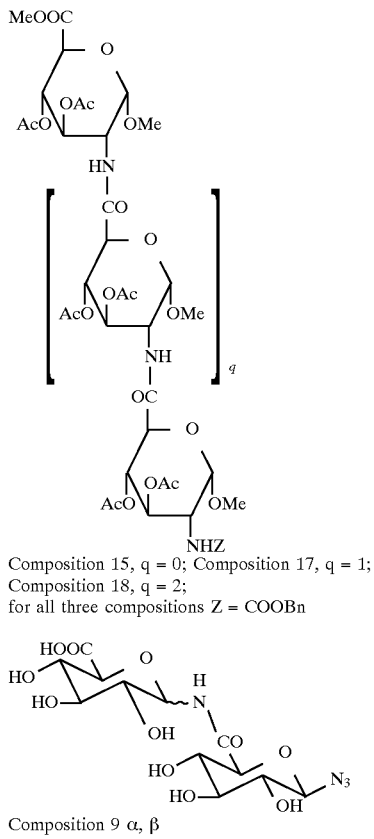

Composition 15, q = 0; Composition 17, q = 1;
Composition 18, q = 2;
for all three compositions Z = COOBn Composition 9 α, β

Example 5

Sulfation of Tetrasaccharopeptide (18)

A solution of composition 18 (100 mg) in a mixture of methanol-water (1:1, 10 ml) with 1M NaOH (0.3 ml) is stirred overnight at room temperature. The mixture was neutralized with AG 50× H+ form ion-exchange resin and the solvent is evaporated to furnish the free hydroxyl containing uronic acid derivative.

A solution of uronic acid derivative in DMF (5 ml) with sulfur trioxide pyridine complex (100 mg) is stirred for 3 days at room temperature. The mixture is neutralized with NaHCO₃ to a pH of about 8, evaporated, desalted on a biogel P-2 column using ammonium bicarbonate (0.5M), the ammonium salt is converted to the sodium salt by passing through a SP-Sephadex ion-exchange column yields the sulfated N-protected tetrasaccharopeptide 19.

Example 6

Solid Phase Synthesis

Composition 13 (427 mg) is deacetylated and hydrogenated as described above to give the free amino derivative (200 mg). The free amine is treated with BOC-ON {2-tert-butoxycarbonyloxy-imino)-2-phenylacetonitrile, 390 mg} in dioxane (10 ml) and triethyl amine (TEA, 0.2 ml), the solvent is evaporated, and the residue is dried, redissolved in pyridine (10 ml), cooled to 0° C. and acetic anhydride (0.5 ml) is added dropwise into the solution. The reaction mixture is stirred overnight, poured into ice-water, extracted with chloroform, evaporated and the residue is recrystallized from ethanol to yield Boc-sugar amino acid methyl ester (380 mg). Selective deesterification of the Boc-derivative, as earlier described, yields methyl 3,4-di-O-acetyl-2-t-butoxycarbonylamino-2-deoxy-α-D-glucopyranosyl uronic acid (20). Composition 20 is linked to the Merrifield resin as described by Merrifield. (Merrifield, R. B., *Biochemistry*, (1964) 3:1385; Erickson, B. W. and Merrifield, R. B., *The Proteins*, Neurath, H. and Hill, R. L. (eds), Vol.2, 3rd edn, Academic Press, New York, 255–527; Barany, G. and Merrifield, R. B., *The Peptides*, Gross, E. and Meienhofer, J. (eds), Vol.2, Academic Press, New York, 3–285.)

The Boc group is removed for further elongation, by treating the N-protected, resin linked sugar with trifluoroacetic acid (0.5 ml) in dichloromethane (20 ml) to give the free amino derivative (21) which was treated with TEA (0.2 ml) in dichloromethane (20 ml). Coupling 20 and 21 using the previously described method yields the resin linked protected disaccharopeptide. The protecting groups are removed as described above, and the saccharopeptide is detached from the resin treating it with hydrogen fluoride as described by Merrifield. (Merrifield, R. B., *Biochemistry*, (1964) 3:1385; Erickson, B. W. and Merrifield, R. B., *The Proteins*, Neurath, H. and Hill, R. L. (eds), Vol.2, 3rd edn, Academic Press, New York, 255–527; Barany, G. and Merrifield, R. B., *The Peptides*, Gross, E. and Meienhofer, J. (eds), Vol.2, Academic Press, New York, 3–285.)

Example 7

N,N'-[bis(β-maltotriosyl)]-succinic diamide sulfate (26)

(a) A solution of maltotriose undecaacetate (1.93 g) in dichloromethane (10 ml) was treated with azidotrimethylsilane (0.4 ml) and tin (IV) chloride (0.18 ml), the reaction mixture was stirred overnight at room temperature, diluted with chloroform (50 ml) and extracted with saturated aqueous sodium bicarbonate, water, dried and evaporated. Column chromatography (toluene-ethyl acetate, 7:3→3:2) gave 1-azido-1-deoxy-(2,3,4,6-tetra-O-acetyl-α-D-glucopyranosyl)-(1→4)-O-(2,3,6-tri-O-acetyl-α-D-glucopyranosyl)-(1→4)-2,3,6-tri-O-acetyl-β-D-glucopyranose (22, 1.82 g, 96%).

A solution of 22 (1.31 g) in ethyl acetate (15 ml), was hydrogenated in the presence of Pd-C (0.3 g) at atmospheric pressure for one hour. Pd-C was filtered, and the solvent was evaporated to give deca-O-acetyl-β-maltotriosyl amine (23, 1.29 g, 100%); $[\alpha]_D$+91.8° (c 1.01, chloroform).

To a solution of 23 (0.89 g) in dichloromethane (10 ml) at 0° C., pyridine (0.085 ml) followed by succinyl dichloride (0.05 ml) were added dropwise. The reaction mixture was stirred overnight at room temperature, diluted with chloroform (50 ml), washed with saturated aqueous NaHCO₃ and water. The organic layer was dried and evaporated, and the crude product was purified by column chromatography (toluene-acetone, 3:2) to yield N,N'-[bis(deca-O-acetyl-β-maltotriosyl)]-succinic diamide (24, 0.93 g, 45%); $[\alpha]_D$+ 93.9° (c 1.28, chloroform).

A solution of 24 (0.49 g) in a mixture of methanol and water (2:1, 9 ml) was treated with methanolic sodium methoxide to adjust the pH to 8. The mixture was stirred overnight at 0° C., and neutralized with AG 50 W-X8 (H+) resin. The resin was filtered, the filtrate was evaporated and the residue was dried in vacuo to yield N,N'-[bis(β-maltotriosyl)]-succinic diamide (25, 0.25 g, 90%).

A solution of 25 (0.19 g) in DMF (5 ml) 2,6-di-t-butyl-4-methylpyridine (1.51 g) was treated with sulfur trioxide pyridine complex (1.16 g) and the mixture was stirred at room temperature for three days. The reaction mixture was cooled to 0° C. and the pH was adjusted to 8 using saturated aqueous NaHCO$_3$, and the solvent was evaporated. The residue was desalted on a Biogel P-2 column using 0.5M ammonium bicarbonate as eluant. The carbohydrate containing fractions were pooled and lyophilized. The resulting product was passed through an SP Sephadex C-25 (Na+) column with water to yield the sodium salt of N,N'-[bis(β-maltotriosyl)]-succinic diamide sulfate (26, 0.52 g, 92%)

(b) NH$_4$HCO$_3$ (6.32 g) was added to a solution of maltotriose (2.02 g) in water, and the mixture was stirred at room temperature. Additional NH$_4$HCO$_3$ (6.32 g) was added after 3 days. TLC (isopropyl alcohol-acetone-water, 4:2:1) indicated complete conversion after one week, and the mixture was liophylized. The resulting maltotriosyl amine (2.02 g) was dissolved in water (10 ml), aqueous NaHCO$_3$ was added to pH 9, the mixture was cooled to 0° C., and succinyl dichloride (0.16 ml) was added dropwise. The mixture was evaporated and the residue was purified by column chromatography (chloroform-90% aqueous methanol, 1:1) to yield 25. Sulfation of 25, as described above yielded 26.

Sulfation of 30, as described above yielded N-[bis(β-maltosyl)]-succinic diamide sulfate (31).

Example 9

N,N'-[bis(β-maltosyl)]-adipic diamide sulfate (34)

A solution of hepta-O-acetyl-β-D-maltosyl amine (0.64 g) and adipic acid (0.07 g) in THF (6 ml) was treated with DIC (0.25 ml) and HOBT (50 mg) as described above, to yield N,N'-[bis(hepta-O-acetyl-β-maltosyl)]-adipic diamide. The crude product was purified by column chromatography (toluene-acetone, 4:1) to give final product 32 (0.24 g, 34%), [α]$_D$ 55.60 (c, 1.00, chloroform).

A solution of 32 (0.24 g) was deacetylated in methanol (10 ml) as described above to give N,N'-[bis(β-maltosyl)]-adipic diamide (33, 0.12 g, 90%).

Sulfation of 33 was carried out as described above to give N,N'-[bis(β-maltosyl)]-adipic diamide sulfate 34.

The structures of compositions 26, 31 and 34 are shown below in formula VII:

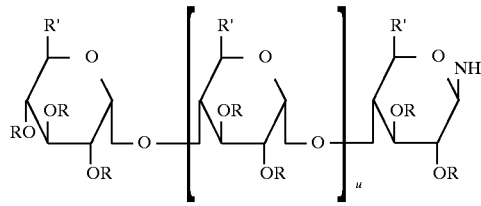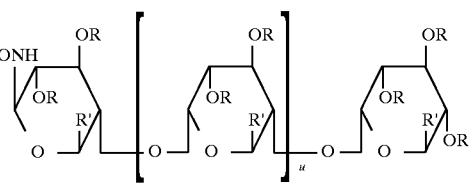

Composition 26, u = 1, t = 2; Composition 31, u = 0, t = 2; Composition 34, u = 0, t = 4;
for all three compositions R = —SO$_3^-$, R' = —CH$_2$OSO$_3^-$

Example 8

N,N'-[bis(β-maltosyl)]-succinic diamide sulfate (31)

A solution of maltose octaacetate (6.78 g) in dichloromethane (50 ml) was treated with azidotrimethylsilane (1.8 ml) and tin (IV) chloride (1.0 ml), and the mixture was stirred overnight at room temperature. The reaction mixture was worked up as described previously and the crude product was recrystallized from ethanol to give 1-azido-1-deoxy-(2,3,4,6-tetra-O-acetyl-α-D-glucopyranosyl)-(1→44)-2,3,6-tri-O-acetyl-β-D-glucopyranose (27, 6.28 g, 95%).

A solution of 27 (0.67 g) in ethyl acetate (15 ml), was hydrogenated in the presence of Pd-C (0.3 g) at atmospheric pressure for one hour. Pd-C was filtered, and the solvent was evaporated to give 1-amino-1-deoxy-(2,3,4,6-tetra-O-acetyl-α-D-glucopyranosyl)-(1→4)-2,3,6-tri-O-acetyl-β-D-glucopyranose (28, 0.64 g, 100%).

A solution of 28 (0.64 g) and succinic acid (0.06 g) in THF (8 ml) was treated with DIC (0.24 ml) in the presence of HOBT (50 mg) and the mixture was stirred for three days at room temperature (TLC—toluene-acetone, 3:2). The solvent was evaporated and the residue was purified by column chromatography (toluene-acetone, 4:1→7:3) to give N,N'-[bis(hepta-O-acetyl-β-maltosyl)]-succinic diamide (29, 0.56 g, 84%).

A solution of 29 (0.34 g) in methanol (20 ml) was treated with methanolic sodium methoxide (pH 9) overnight at 0° C. The product crystallized spontaneously from the solution, was filtered and washed with cold methanol to furnish N,N'-[bis(β-maltosyl)]-succinic diamide (30, 0.18 g, 95%).

Example 10

N,N'-[bis(β-D-cellobiosyl)]-succinic diamide sulfate (39)

A solution of cellobiose octaacetate (6.78 g) in dichloromethane (50 ml) was treated with azidotrimethylsilane (1.8 ml) and tin (IV) chloride (1.0 ml), and the mixture was stirred overnight at room temperature. The reaction mixture was worked up as described previously and the crude product was recrystallized from ethanol to give 1-azido-1-deoxy-(2,3,4,6-tetra-O-acetyl-β-D-glucopyranosyl)-(1→4)-2,3,6-tri-O-acetyl-β-D-glucopyranose (35, 6.48 g, 98%).

A solution of 35 (0.67 g) in ethyl acetate (15 ml) was hydrogenated in the presence of Pd-C (0.3 g) at atmospheric pressure for one hour. Pd-C was filtered, and the solvent was evaporated to give 1-amino-1-deoxy-(2,3,4,6-tetra-O-acetyl-β-D-glucopyranosyl)-(1→4)-2,3,6-tri-O-acetyl-β-D-glucopyranose (36, 0.64 g, 100%).

A solution of 36 (0.64 g) and succinic acid (0.06 g) in THF (8 ml) was reacted with DIC (0.24 ml) in the presence of HOBT (50 mg) as described above to give N,N'-[bis (hepta-O-acetyl-β-cellobiosyl)]-succinic diamide (37, 0.58 g, 86%), [α]$_D$–7.1° (c, 1.00, chloroform).

A solution of 37 (0.19 g) in methanol (10 ml) was deacetylated as described above, to yield the crystalline N,N'-[bis(β-cellobiosyl)]-succinic diamide (38, 0.1 g, 98%), [α]$_D$–18.4° (c 0.98, water).

Sulfation of 38 (0.05 g) as described above yielded N,N'-[bis(β-D-cellobiosyl)]-succinic diamide sulfate (39, 0.25 g, 89%).

The structure of composition 39 is as follows in formula VIII:

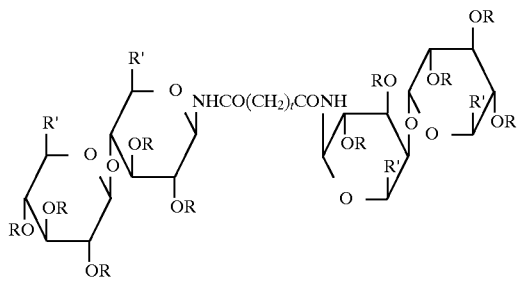

Composition 39: t = 2, R = —SO$_3^-$, R' = —CH$_2$OSO$_3$

Example 11

N,N'-[bis(β-D-cellobiosyl)]-3-hydroxy-3-methylglutaric diamide sulfate (42)

Hepta-O-acetyl-β-D-cellobiosyl amine (0.64 g) and 3-hydroxy-3-methylglutaric acid (0.08 g) was reacted in 1,4-dioxane (8 ml) with DIC (0.24 ml) in the presence of HOBT (50 mg) as described above to give N,N'-[bis(hepta-O-acetyl-β-cellobiosyl)]-3-hydroxy-3-methylglutaric diamide (40, 0.53 g, 76%), [α]$_D$–11.7° (c 1.06, chloroform).

A solution of 40 (0.34 g) in methanol (10 ml) was deacetylated as described above, yielded the crystalline N,N'-[bis(β-cellobiosyl)]-3-hydroxy-3-methylglutaric diamide (41, 0.19 g, 98%), [α]$_D$–4.8° (c 1.03, water).

Sulfation of 41 (0.16 g) as described above yielded N,N'-[bis(β-D-cellobiosyl)]-3-hydroxy-3-methylglutaric diamide sulfate (42, 0.41 g, 91%).

The structure of composition 42 is as follows in formula IX:

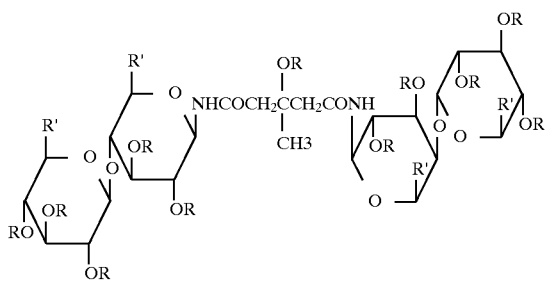

Composition 42: R = —SO$_3^-$, R' = —CH$_2$OSO$_3$

Example 12

β-Glucuronidase Inhibition Assay

Composition 9β was used to measure the β-glucuronidase activity, and the measurement was performed in the same manner as that of the conventional method.

The procedure was carried out according to instructions provided in the Sigma kit 325-A. The reagents used were provided in the kit and the proportions of the reagents used is described in the table below:

TABLE 1

| Assay/Reagent | Blank | Control | 9β |
|---|---|---|---|
| Enzyme (μl) | 2 | 2 | 2 |
| Acetate buffer* (μl) | 3 | 3 | 3 |
| PGA# (μl) | — | 10 | 10 |
| 9β (50 mM, μl) | — | — | 15 |
| Water (μl) | 25 | 15 | — |

*0.2M sodium acetate buffer, pH 4.5 at 25° C.;
30 mM phenolphthalein glucuronic acid (PGA), pH 4.5 at 25° C.

All components, except PGA, were pre-incubated at room temperature for 30 min, PGA was then added to the mixture. At various time points (0.5, 1 and 2h), 2 μl aliquots were removed and added to 1 ml assay diluent, mixed and absorbance read at 550 nm against the blank (A$_{550}$). The assay diluent is a mixture of acetate buffer (1.44 ml), water (0.96 ml) and AMP (2-amino-2-methyl-1-propanol) buffer (12 ml, 0.1M AMP, pH 11, containing 0.2% sodium lauryl sulfate).

Table 2 lists the results of the assay in terms of the A$_{550}$ values

TABLE 2

| Time (h) | 9β | Control |
|---|---|---|
| 0.5 | 0.014 | 0.104 |
| 1.0 | 0.030 | 0.199 |
| 2.0 | 0.059 | 0.396 |

Composition 9β reduced β-glucuronidase activity by about 85%.

As shown in Table 2, the saccharopeptides of the instant invention are inhibitors of the β-glucuronidase, and would be useful in the purification of the enzyme by affinity chromatography using standard methods.

Example 13

Effect of Saccharopeptides on Cell Binding and Proliferation

The effect of compositions 26 on the binding of RO-12 UC cells to bFGF coated micro-titer wells was determined as described by Ishihara, M., et al., Anal Biochem (1992) 202:310–315. (Also see U.S. Pat. No. 5,296,471, issued Mar. 22, 1994). Bound cells are readily quantitated as total protein. Heparin which inhibits RO-12 UC cell binding was run as a positive control.

The assay was run as follows: Fifty microliters of 10 μg/ml human recombinant bFGF was added to wells of a 96-well tissue culture plate and incubated overnight at 4° C. The wells were aspirated with PBS to remove any unbound bFGF, rinsed twice with PBS, and subsequently incubated with PBS containing 5% (v/v) fetal bovine serum for 1 hour at room temperature. RO-12 UC cells were suspended at a density of 3×10$^6$ cells/ml in PBS containing 5% fetal bovine serum. To this mixture was added the desired amount of sulfated composition, or heparin. They were made up in PBS plus 2.5% fetal bovine serum. A control was also run, containing only PBS plus 2.5% fetal bovine serum. Next, 100 μl of the cell suspension was immediately added to the microtiter wells, and incubated for 5 minutes, after which the wells were washed 3 times with PBS. Finally, the amount of cell protein bound to the wells was determined by dissolving the bound cells in 20 μl of 5% SDS and measuring the protein concentration of the cell lysates. BSA was used as the standard.

To extend the effects seen with RO-12 UC cells, a second experiment was conducted. The capacity of the sulfated maltohexaoses to inhibit the proliferation of a bFGF-dependent adrenocortical endothelial (ACE) cell line was determined. This cell line (provided by D. Gospodarowicz, UCSF) requires either aFGF or bFGF for a proliferative response. Cells were seeded at low density in microtiter wells in the presence of 2 ng/ml bFGF, and growth was determined as total protein after four days in the presence of the sulfated maltohexaoses.

The APTT values of composition 26 were determined as described in U.S. Pat. No. 5,296,471. Table 3 lists the results for the UC-PBA assay, the ACE cell growth inhibition assay, and the APTT values respectively.

Composition 26 is comparable to heparin for bFGF binding activity in the UC-PBA assay ($IC_{50}$ 1 μg/mL. Composition 26 is active in the ACE cell growth inhibition assay. The APTT value of composition 26 was significantly lower than that of other compounds of similar size.

TABLE 3

| Assay | Result |
|-------|--------|
| UC-PBA | 1 μg/ml |
| ACE | + |
| APTT | 14.2% |

While the present invention is disclosed by reference to the details of above examples, it is to be understood that this disclosure is intended in an illustrative rather than limiting sense, as it is contemplated that modifications will readily occur to those skilled in the art, within the spirit of the invention and the scope of the appended claims.

What is claimed is:

1. A saccharopeptide of formula (I):

$$W-[Y-W-]_m \quad (I)$$

wherein:
each W is independently one or more saccharides, independently selected from the group consisting of glucose, galactose, glucuronic acid, galactosamine, maltose and cellobiose;
said saccharide(s) comprising hydroxyl or amine groups, said groups being optionally substituted with —H, halogen, —COOH, or —$OR^1$; wherein any hydroxyl groups of said saccharides are optionally sulfated;
wherein $R^1$ is selected from the group consisting of alkyl, aryl, aralkyl, acyl, —$SO_3$, —$PO_3$, protecting groups, lipids, amino acids, and peptide chains;
each Y is independently selected from the group consisting of —CO—NH— or —NH—CO—;
m is an integer from 1 to 5; and
the saccharopeptide has a molecular weight of up to 10 kDa; with the provisos that:
  a) when m is 1, then W is not a monosaccharide; and
  b) if a W group is greater than one saccharide, then said saccharides are independently covalently linked by ether, thioether, glycosidic, thioglycosidic, or amino bonds.

2. A method for treating an animal, including humans, for disease wherein said disease is selected from the group consisting of cardiovascular disease, retinopathies, and cancer, comprising:
Administering to said animal an effective amount of a composition comprising the formula (I):

$$W-[Y-W-]_m \quad (I)$$

wherein
W is independently one or more saccharide(s);
Y is independently —CO—NH— or —NH—CO—; and
M is an integer greater than or equal to one; and the saccharopeptide has a molecular weight up to 10 kDa.

3. A method for treating or preventing inflammation in an animal in need thereof, comprising:
administering to said animal an effective amount of a compound of the formula (I):

$$W-[-Y-W-]_m \quad (I)$$

wherein
W is independently one or more saccharide(s);
Y is independently —O—NH or —NH—CO—; and
m is an integer greater than or equal to one; and the saccharopeptide has a molecular weight up to 10 kDa.

* * * * *